United States Patent
Zarins et al.

(10) Patent No.: US 7,131,991 B2
(45) Date of Patent: Nov. 7, 2006

(54) ENDOLUMINAL PROSTHETIC ASSEMBLY AND EXTENSION METHOD

(75) Inventors: Christopher K. Zarins, Portola Valley, CA (US); Scott A. Doig, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 401 days.

(21) Appl. No.: 10/131,975

(22) Filed: Apr. 24, 2002

(65) Prior Publication Data

US 2003/0204242 A1  Oct. 30, 2003

(51) Int. Cl.
*A61F 2/06* (2006.01)
(52) U.S. Cl. .................................... 623/1.13; 623/1.35
(58) Field of Classification Search ............... 623/1.35, 623/1.36, 1.15
See application file for complete search history.

(56) References Cited

U.S. PATENT DOCUMENTS

| | | | |
|---|---|---|---|
| 5,607,464 A | | 3/1997 | Trescony et al. |
| 5,609,627 A | * | 3/1997 | Goicoechea et al. ........ 623/1.35 |
| 6,093,203 A | | 7/2000 | Uflacker |
| 6,102,938 A | * | 8/2000 | Evans et al. ................ 623/1.35 |
| 6,143,022 A | | 11/2000 | Shull et al. |
| 6,383,171 B1 | * | 5/2002 | Gifford et al. ............. 623/1.36 |
| 6,409,756 B1 | * | 6/2002 | Murphy ....................... 623/1.35 |
| 6,663,667 B1 | * | 12/2003 | Dehdashtian et al. ...... 623/1.35 |

FOREIGN PATENT DOCUMENTS

| | | |
|---|---|---|
| WO | WO 9926559 A | 6/1999 |
| WO | WO 0121102 A | 3/2001 |

\* cited by examiner

*Primary Examiner*—Anhtuan T. Nguyen
*Assistant Examiner*—Sarah Webb
(74) *Attorney, Agent, or Firm*—Anthony A. Sheldon

(57) ABSTRACT

An endoluminal prosthetic assembly includes a trunk body including first and second elongated branches. The trunk body and elongated branches include a bifurcated body lumen formed therein. The assembly further includes an extension cuff including a cuff branch and an access port. The extension cuff, cuff branch, and access port include a bifurcated cuff lumen formed therein. A portion of the extension cuff is retainably positioned within the trunk body. A portion of the cuff branch is retainably positioned within one of the elongated branches. The cuff lumen is in communication with the body lumen. A method of extending an endoluminal prosthetic assembly deployed in a bifurcated vessel is also provided. The assembly includes a trunk body including first and second elongated branches. A portion of a compressed extension cuff is positioned within the trunk body and the first elongated branch. The compressed extension cuff is expanded into operable engagement with the trunk body and the first elongated branch.

20 Claims, 5 Drawing Sheets

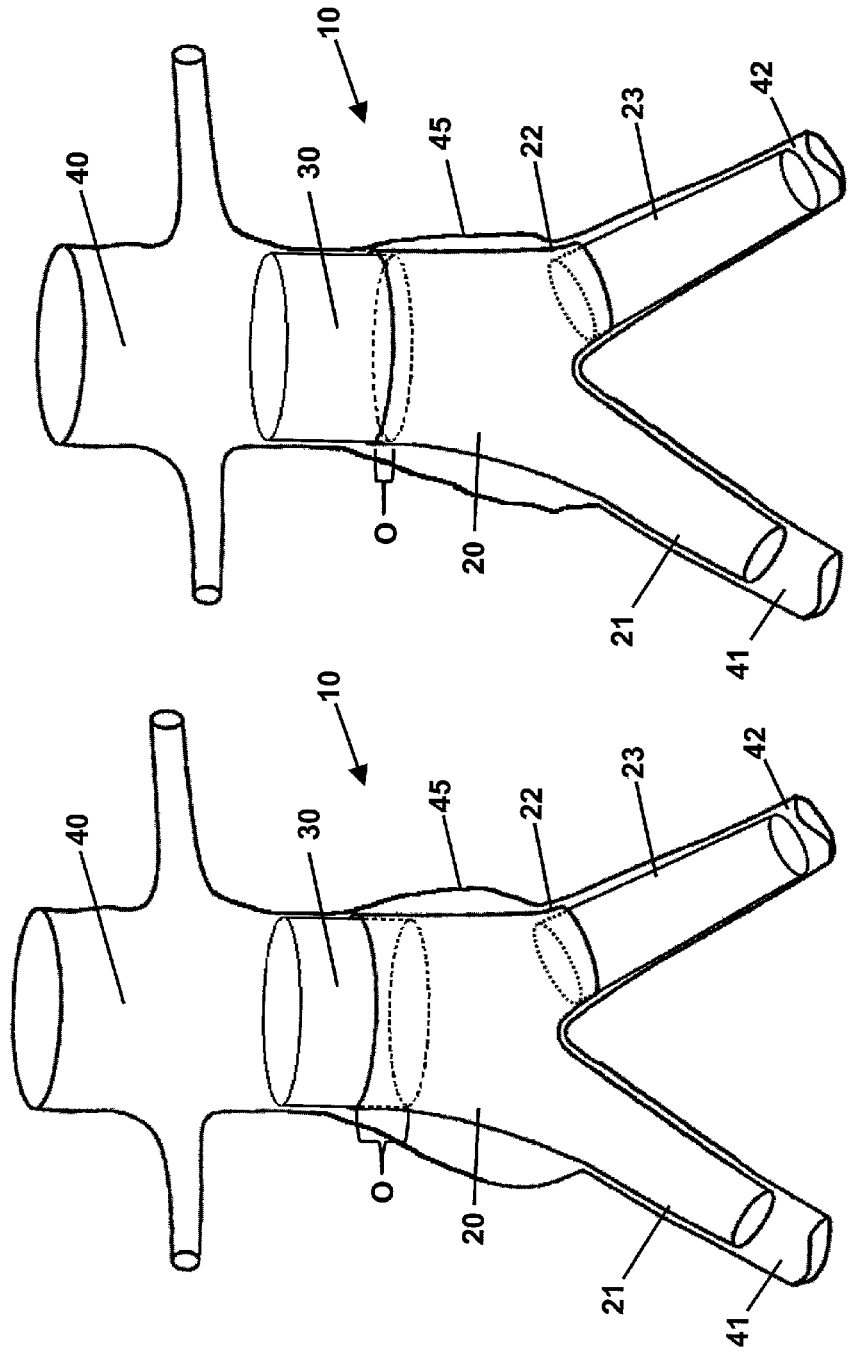

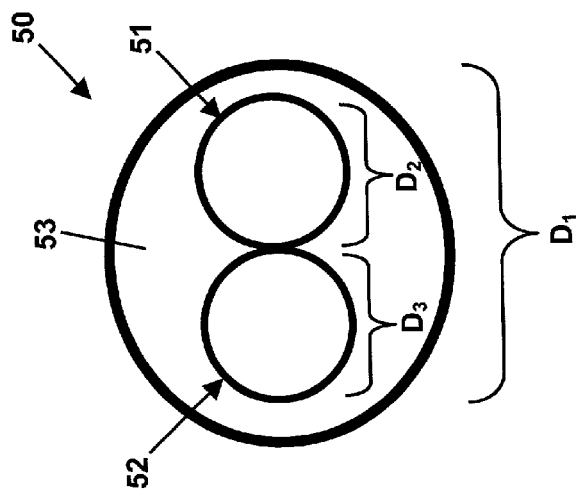
FIG. 2B – Top View
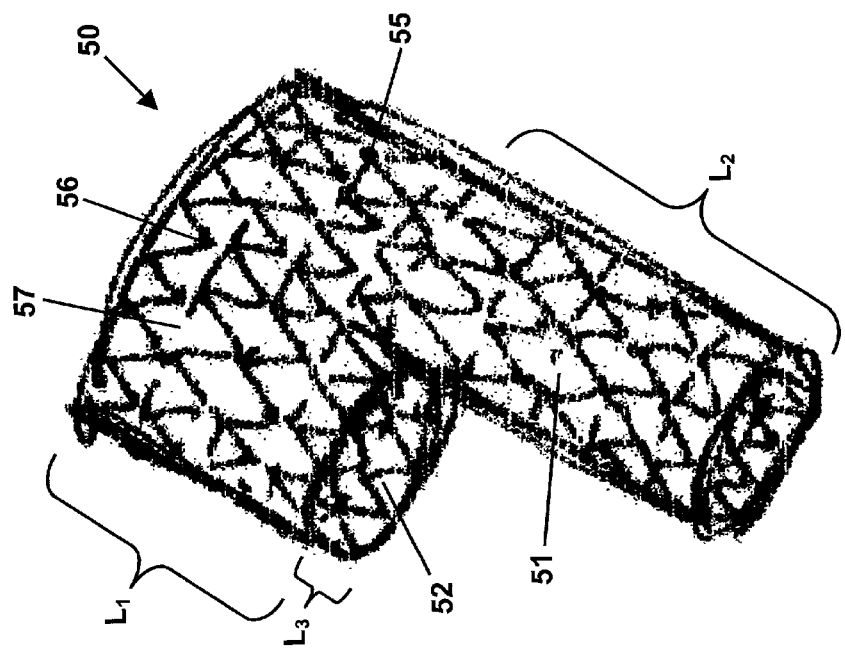
FIG. 2A – Side View

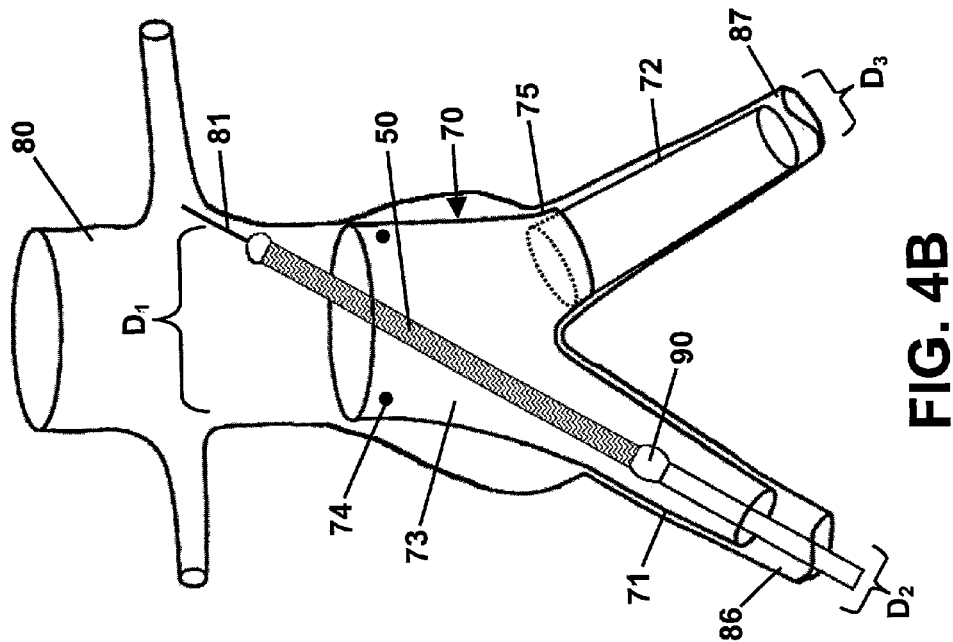
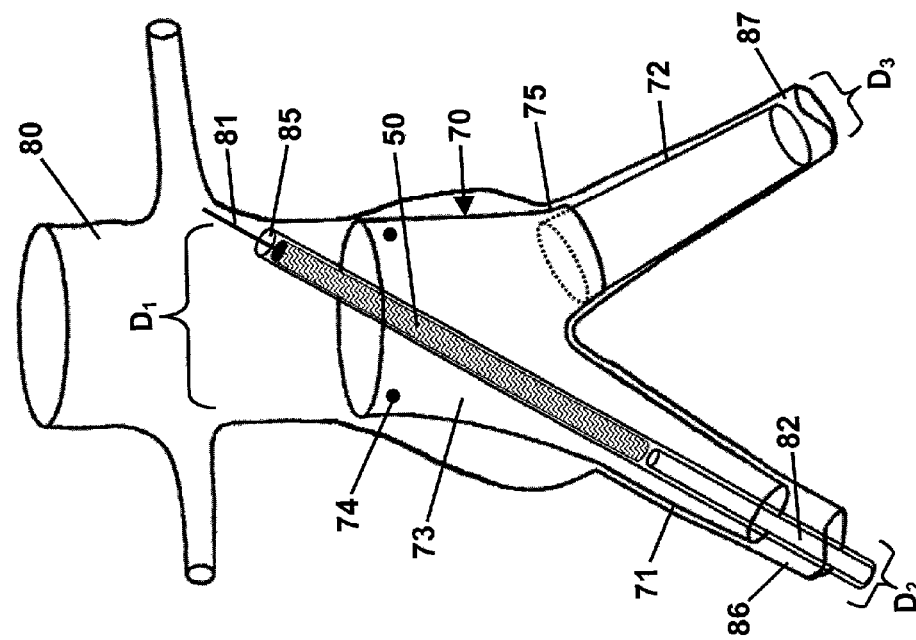

ENDOLUMINAL PROSTHETIC ASSEMBLY AND EXTENSION METHOD

TECHNICAL FIELD OF THE INVENTION

The present invention relates generally to the field of implantable medical devices. More particularly, the invention relates to a bifurcated endoluminal prosthetic assembly and a method of extension.

BACKGROUND OF THE INVENTION

Abdominal aortic aneurysms (AAA) represent one of the most common types of aneurysms and result in about 15,000 deaths annually in the United States. An aneurysm is produced when a thinning or weak spot in a vessel wall dilates eventually posing a health risk from its potential to rupture, clot, or dissect. An aneurysm frequently occurs in arteries, but may also form in veins. The etiology of aneurysm formation is not entirely understood, but is thought to be related to congenital thinning of the artery, atherosclerotic vessel degeneration, vessel trauma, infection, smoking, high blood pressure, and other causes leading to vessel degeneration. Left untreated, AAA may lead to gradual vessel expansion, thrombus formation leading to stroke or other vessel blockage, vessel rupture, shock, and eventual death.

AAA are generally localized on long abdominal aortic sections below the renal arteries and oftentimes extend into one or both of the iliac arteries. The aneurysm may begin with a small vessel distension that progressively enlarges at a variable and unpredictable rate. An AAA may enlarge at an average rate of about 0.3–0.5 cm per year. The AAA may continue to enlarge in a silent fashion until a catastrophic event, such as a rupture, occurs. The best predictor of rupture risk is size, wherein rupture is relatively uncommon in AAA less than 5 cm. Once reaching about 8 cm, however, there is about a 75 percent chance of rupture within a year. Besides rupture, another risk of AAA is thrombus dissection. As the vessel enlarges, a thrombus may develop in the aneurysm due to perturbations in blood flow dynamics. Pieces of the clot may eventually loosen and carry away, eventually forming blockages in the legs, lungs, or brain.

AAA are most commonly treated in open surgical procedures, where the diseased vessel segment is bypassed and repaired with an artificial vascular graft. While considered to be an effective surgical technique, particularly considering the alternative of the usually fatal ruptured AAA, conventional vascular graft surgery suffers from a number of disadvantages. The surgical procedure is complex and requires experienced surgeons and well equipped surgical facilities. Even with the best surgeons and equipment, patients suffering from such aneurysms are often elderly and weakened from cardiovascular and other diseases. This factor reduces the number of patients eligible for surgery. Even for eligible patients prior to rupture, conventional aneurysm repair has a relatively high mortality rate, usually from 2 to 10%. Morbidity related to the conventional surgery includes myocardial infarction, renal failure, impotence, paralysis, and other conditions. Even with successful surgery, recovery takes several weeks and often requires a lengthy hospital stay.

To overcome some of the drawbacks associated with open surgery, a variety of endovascular prosthesis placement techniques have been proposed. Without the need for open abdominal surgery, patient complications and recovery time may be significantly reduced. One endovascular AAA repair technique involves a tubular prosthesis deployed by remote insertion through a femoral artery. The prosthesis may include a synthetic graft sheath body supported by an expandable structure such as a stent. The stent may be self-expanding or balloon-expanding and typically includes means for anchoring the prosthesis to the vessel wall. The stent-graft acts as a shunt to carry blood flow from a healthy portion of the aorta, through the aneurysm, and into one or both of the iliac artery branches. The prosthesis excludes any thrombus present in the aneurysm while providing mechanical reinforcement of the weakened vessel reducing the risk of dissection and rupture, respectively.

A number of endovascular AAA stent-graft prosthesis designs are known. For aneurysms proximal to the iliac arteries, many of the designs utilize bifurcated structures. Bifurcated stent-graft prostheses generally have a trunk portion with a relatively large lumen deployed in the aorta, and first and second branch portions with smaller branch lumens deployed within each of the iliac arteries. The deployed trunk and branch portions preferably seal to each other and to the healthy vascular walls beyond the aneurysm to isolate the aneurysm from the bloodstream. Advantageously, the aortic blood flow enters the trunk prosthetic lumen, is separated into the two branch prosthetic lumens, and then flows into each of the iliac arteries in a path that approximates that of a normal, healthy vascular system.

In certain situations, it is desirable to extend the length of the deployed prosthesis trunk portion and provide a seal further up the aorta, into healthy vascular tissue. Failing to do so may result in leakage into the aneurysm. Trunk extension may be warranted after prosthesis migration resulting from morphological changes in the aneurysm, or during prosthesis deployment in a tortuous vessel. The trunk extension may be performed after the AAA repair procedure, as with prosthesis migration, or during the initial procedure, as with a tortuous vessel. Extension may be accomplished by deploying a tubular shaped extension cuff partially within the trunk body. The deployed extension cuff may extend the effective length of the prosthesis and provide a seal to healthy vascular tissue. Multiple extension cuffs may be used in series to further extend the prosthesis length or to negotiate particularly tortuous vessel paths.

An extension cuff is generally a stent-graft device that allows adjustment of the length of the implanted bifurcated prosthesis. The extension cuff may expand to a diameter slightly larger than the prosthesis trunk portion thereby providing sealed attachment between the trunk and cuff. Frictional forces between the overlapping surfaces usually prevent the cuff from detaching from the primary stent-graft module. At its other end, the extension cuff may seal against healthy vascular tissue minimizing blood flow into the aneurysm. Such deployment of the second branch can be very straightforward and in situ deployment of a bifurcated prostheses and extension cuff appears to hold significant promise for many AAA patients.

One shortcoming associated with the extended prosthetic stent-graft relates to extension cuff separation. The AAA may vary widely in location, size, and the distended shape of the aneurysm itself. Particularly after treatment, the aneurysm and associated vessels may drastically change morphology thereby exerting stress forces on the deployed prosthesis. A significant amount of stress may be exerted on the joint between the trunk portion and the extension cuff. Multiple extension cuffs used in series may be particularly vulnerable to such stresses due to the presence of multiple joints. With sufficient change in aneurysm morphology and subsequent stress placed on the joint(s), the extension cuff may separate from the prosthesis. The patient may have to undergo another treatment given the problem is detected early. Undetected module separation may lead to continued leakage, aneurysm regrowth, and even the more serious problems associated with AAA. Accordingly, it would be advantageous to prevent separation of the extension cuff from the endoluminal prosthesis.

Therefore, it would be desirable to provide a bifurcated endoluminal prosthetic assembly and a method of extending an endoluminal prosthetic assembly that overcomes the aforementioned and other disadvantages.

SUMMARY OF THE INVENTION

An aspect according to the present invention provides an endoluminal prosthetic assembly. The assembly includes a trunk body including first and second elongated branches. The trunk body and elongated branches include a bifurcated body lumen formed therein. The assembly further includes an extension cuff including a cuff branch and an access port. The extension cuff, cuff branch, and access port include a bifurcated cuff lumen formed therein. A portion of the extension cuff is retainably positioned within the trunk body. A portion of the cuff branch is retainably positioned within one of the elongated branches. The cuff lumen is in communication with the body lumen. The extension cuff may include at least one aperture formed in the extension cuff allowing fluid flow through said aperture. The extension cuff may include a crown portion operably attached to the extension cuff, wherein the crown allows fluid flow through crown openings formed therein. The crown may include a crown diameter greater than a vessel diameter. The extension cuff may include at least one marker. The extension cuff may include a biocompatible membrane disposed on a support element. The extension cuff may include an expandable extension cuff, wherein the expandable extension cuff expands from a collapsed form to an expanded ring form. The expandable extension cuff may be a self-expanding extension cuff or a balloon-expandable extension cuff. The expandable extension cuff may have an extension cuff diameter greater than a trunk body diameter. The expandable extension cuff may have a cuff branch diameter greater than a first elongated branch diameter.

Another aspect according to the invention provides a method of extending an endoluminal prosthetic assembly deployed in a bifurcated vessel. The assembly includes a trunk body including first and second elongated branches. A portion of a compressed extension cuff is positioned within the trunk body and the first elongated branch. The compressed extension cuff is expanded into operable engagement with the trunk body and the first elongated branch. The compressed extension cuff may be self-expanded or balloon-expanded. The operable engagement may include frictional surface contact. Fluid egress may be provided through the extension cuff.

Another aspect according to the invention provides an endoluminal prosthetic assembly. The assembly includes a trunk body including first and second elongated branches deployed in a bifurcated vessel. The assembly further includes means for positioning a portion of a compressed extension cuff within the trunk body and the first elongated branch, and means for expanding the compressed extension cuff into operable engagement with the trunk body and the first elongated branch.

BRIEF DESCRIPTION OF THE DRAWINGS

FIGS. 1A and 1B are sequential views of a prior art endoluminal prosthetic assembly including extension cuff deployed in an abdominal aortic aneurysm;

FIGS. 2A and 2B are side and top perspective views of an extension cuff in accordance with the present invention;

FIGS. 4A and 4B are schematic views of an endoluminal prosthetic assembly being deployed in an abdominal aortic aneurysm with alternate devices.

DETAILED DESCRIPTION

Figure 3B:
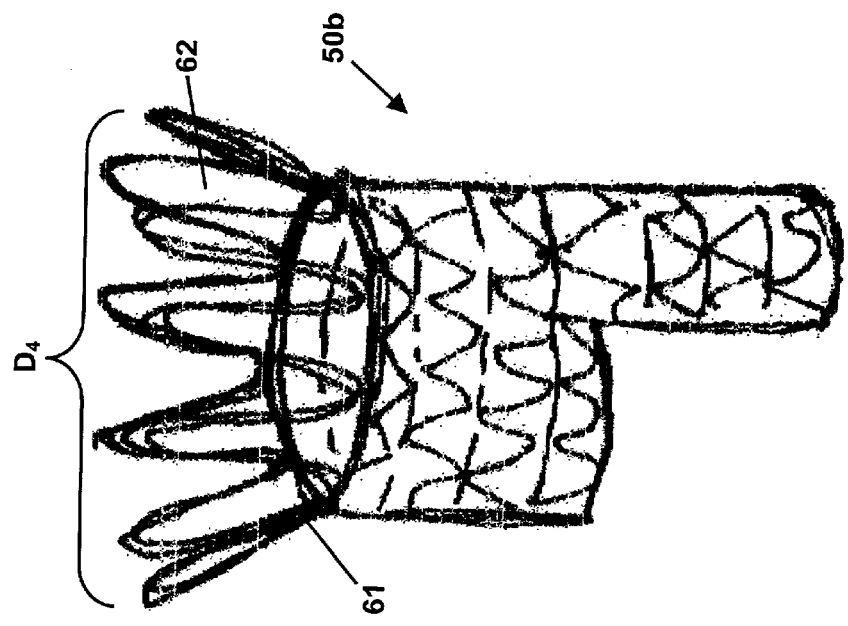
FIGS. 3A and 3B are side perspective views of alternative embodiments of an extension cuff in accordance with the present invention.

Referring to the drawings, wherein like reference numerals refer to like elements, FIGS. 1A and 1B are sequential views of a prior art endoluminal prosthetic assembly 10 including extension cuff 30 deployed in an abdominal aortic aneurysm 45. Assembly 10 includes a tubular trunk body 20, a first branch body 21, and a shortened branch body 22. A second branch body 23 is operably attached to the shortened branch body 22. Trunk body 20 includes a relatively large lumen and is deployed in patient abdominal aorta 40. Trunk body 20 lumen bifurcates into smaller branch lumens of the first branch body 21 and second branch body 23. The branch bodies 21, 23 are deployed within first iliac artery 41 and second iliac artery 42. The deployed trunk body 20 and branch bodies 21, 23 preferably seal to each other and to the healthy vascular walls beyond the aneurysm 45 isolating the aneurysm 45 from the bloodstream. As previously described, aortic blood flow that enters the trunk body 20 lumen is separated into the two branch portions 21, 23, and then flows into each of the iliac arteries 41, 42 in a path that approximates that of a normal, healthy vascular system.

As shown in FIG. 1A, extension cuff 30 is positioned partially within trunk body 20 and preferably seals to the trunk body 20 and abdominal aorta 40. Extension cuff 30 is retained by its mutual surface overlap length, O, with trunk body 20. Frictional forces between the overlapping surfaces usually prevent the extension cuff 30 from detaching from the trunk body 20. Multiple extension cuffs (not shown) may be serially positioned to provide additional extension and/or negotiate tortuous vessel paths.

As shown in FIG. 1B, the site may undergo morphological changes as the aneurysm 45 heals. These changes may produce stress forces on the assembly 10. For example, trunk body 20 may be pulled in an opposite direction from the extension cuff 30. As a result, the mutual surface overlap length, O, may shorten. Continued changes in aneurysm 45 morphology may result in further surface overlap length, O, reduction and eventual separation of extension cuff 30 from trunk body 20. Surface overlap length, O, reduction and component separation, may result in leakage of blood into the aneurysm 45.

Referring now to side and top views FIGS. 2A and 2B, an extension cuff 50 configured in accordance with the present invention is shown. Extension cuff 50 includes a cuff branch 51 and an access port 52. The extension cuff 50, cuff branch 51, and access port 52 include a bifurcated cuff lumen 53 formed therein. The size and geometry of the extension cuff 50 may vary, but is generally adapted to be received by and seal to a deployed endoluminal prosthesis. In one embodiment, the extension cuff 50 may be tubular in shape and the access port 52 may be a truncated cuff branch. In another embodiment, the access port 52 may extend a longer distance up to the length of the cuff branch 51.

Cuff lumen 53 may extend into and through cuff branch 51 and access port 52, providing a path for blood flow. At least one marker 55 may be disposed on the extension cuff 50, cuff branch 51, and/or access port 52 facilitating positioning of extension cuff 50 in situ. In one embodiment, marker 55 may be a radiopaque marker visualized by fluoroscopy. Those skilled in the art will recognize that the size, nature, number, and geometry of the marker 55, as well as the method of visualization, may vary to provide effective extension cuff 50 positioning.

Extension cuff 50 may be formed from a variety of materials used for expandable prosthetic devices known in the art. For example, extension cuff 50 may include covered stent design elements disclosed in U.S. Pat. No. 6,143,022 issued to Shull et al. Extension cuff 50 may further include pleated structure design elements disclosed in U.S. Pat. No. 5,607,464 issued to Trescony et al. Cuff branch 51 and access port 52 may be formed from like materials as extension cuff 50. Those skilled in the art will recognize that extension cuff 50 geometry, size, and construction may vary without diminishing the utility of the present invention.

Extension cuff 50 may be formed from a plurality of support elements 56, such as a mesh of wires welded together at points of contact. Support elements 56 may be manufactured from a resilient material known in the art, such as nitinol, titanium, tantalum, stainless steel, metal alloy, polymer, and other biocompatible material capable of maintaining an expanded shape inside the vessel in which the device is deployed. Graft material 57 may be disposed outside or inside of the support elements 56. Graft material 57 may include any number of biocompatible, blood-impermeable graft membranes known in the art, such as polyester, polyethylene, polytetrafluoroethylene (PFTE), polyurethane, propylene, nylon, and the like. Graft material 57 may be secured to support elements 56 with a variety of strategies known in the art. Examples include suturing, adhesive bonding, heat welding, ultrasonic welding, and the like.

The extension cuff 50, cuff branch 51, and access port 52 may expand from a collapsed form into an expanded form facilitating intravascular deployment. In one embodiment, as shown in FIGS. 2A and 2B, extension cuff 50 may have a deployed diameter, D1, of about 15 to 30 mm and a deployed length, L1, of about 20 to 100 mm. Cuff branch 51 may have a deployed diameter, D2, of about 5 to 15 mm, and deployed length, L2, of about 10 to 160 mm. Access port 52 may have a deployed diameter, D3, of about 5 to 15 mm, and deployed length, L3, of about 0 to 160 mm. In another embodiment, deployed diameter, D1, and length, L1, may be chosen in dependency of the intact infrarenal aorta portion position upstream of an AAA, the position of the renal arteries, the internal diameter of the deployed endoluminal prosthesis trunk body, and/or tortuous nature of the vessel. For example, extension cuff 50 deployed diameter, D1, may be slightly greater than trunk body inner diameter thereby providing means for extension cuff 50 retention.

Deployed diameters, D2 and D3, and lengths, L2 and L3, may be chosen in dependency of the internal diameter(s) and length(s) of the deployed endoluminal prosthesis elongated branch portions. For example, cuff branch 51 deployed diameter, D2, may be greater than first elongated branch inner diameter thereby providing means for cuff branch 51 retention. In yet another embodiment, extension cuff 50 deployed diameter and length, D1 and L1, maybe varied as required for deployment in a vessel other than an abdominal aorta. Furthermore, cuff branch 51 and access port 52 need not have equivalent deployed diameters and lengths. Those skilled in the art will recognize that the dimensions of the extension cuff 50, cuff branch 51, and access port 52 may vary as required by application.

Figure 3A:
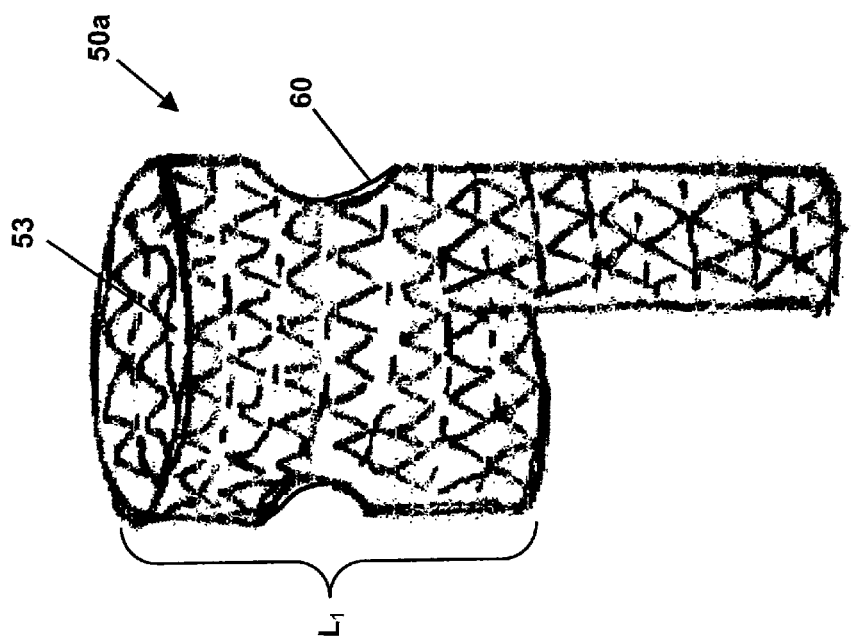

Referring now to side perspective views perspective views FIGS. 3A and 3B, showing alternative embodiments of an extension cuff 50a, 50b. The alterative embodiment extension cuffs 50a, 50b include means for fluid egress. Fluid egress may be necessary when the extension cuff is positioned adjacent a branched vessel. For example, it may be desirable to provide a path for blood to flow into the renal arteries from within the extension cuff.

As shown in FIG. 3A, extension cuff 50a may include at least one aperture 60 formed therein allowing fluid flow. The two apertures 60 shown may allow blood to flow from the cuff lumen 53 to both of the renal arteries when the extension cuff 50 is in position to cover the renal arteries. The aperture 60 may permit use of a longer extension cuff length since vessel blockage is not an issue. Using a longer extension cuff deployed length, L1, may eliminate the need for deploying multiple extension cuffs.

As shown in FIG. 3B, extension cuff 50b may include a crown 61 portion operably attached to the extension cuff. Crown 61 allows fluid flow through crown openings 62 formed therein. In one embodiment, crown 61 may be manufactured from a bare stent ring allowing fluid to flow through. In another embodiment, crown proximal end deployed diameter, D4, is greater than the internal diameter of the intact infrarenal aorta vessel. A large crown proximal end deployed diameter, D4, may provide means for securing the extension cuff to a vessel wall.

FIGS. 4A and 4B are schematic views of an endoluminal prosthetic assembly being deployed in an abdominal aortic aneurysm with alternate devices, made in accordance with the present invention. Those skilled in the art will recognize that deployment of the endoluminal prosthetic assembly is not limited to the described strategy. Numerous modifications, substitutions, and variations may be made to the strategy while providing effective endoluminal prosthetic assembly deployment consistent with the present invention.

A trunk body 70 is shown already deployed in an abdominal aorta 80. Trunk body 70 may be deployed in vessel by one of many techniques known in the art including intravascular and open surgical methods. Trunk body 70 includes a first elongated branch 71 and a second elongated branch 72. Trunk body 70 and elongated branches 71, 72 include a bifurcated body lumen 73 formed therein. Trunk body 70 may be positioned substantially within abdominal aorta 80. Elongated branches 71, 72 may extend into and seal to first and second iliac arteries 86, 87. In one embodiment, trunk body 70 and elongated branches 71, 72 may be tubular in shape thus approximating the general shape of the vessel in which they are deployed. In another embodiment, second elongated branch 72 may be retainably positioned partially within a shortened branch 75. Those skilled in the art will recognize that numerous strategies for sealably retaining the second elongated branch 72 to the shortened branch 75 may be used with the present invention. In addition, numerous trunk body 70 and elongated branch 71, 72 designs may be used with the present invention.

Trunk body 70 and elongated branches 71, 72 may be formed from a variety of materials used for expandable prosthetic devices known in the art. In one embodiment, trunk body 70 and elongated branches 71, 72 may be formed from like previously described materials and structural elements of extension cuff 50. At least one marker 74 may be disposed on the trunk body 70, first elongated branch 71, and/or second elongated branch 72 facilitating positioning of trunk body 70 in situ. In one embodiment, marker 74 may be a radiopaque marker visualized by fluoroscopy. After proper trunk body 70 and elongated branch 71, 72 deployment, extension cuff 50 may be deployed to extend the endoluminal prosthetic assembly. Deployment may be performed in a variety of techniques known in the art. Extension cuff 50 may be deployed in the same or a separate procedure as trunk body 70.

As shown in FIG. 4A, extension cuff 50 may be compressed within a flexible catheter 85 or other adequate delivery device as known in the art. In another embodiment shown in FIG. 4B, extension cuff 50 may be compressed and disposed on an expandable balloon catheter 90 for deployment. In yet another embodiment, extension cuff 50 may be deployed during open surgery. Those skilled in the art will recognize that the extension cuff 50 may be deployed through numerous pathways (e.g., through elongated branch 71, 72 or abdominal aorta 80), however, deployment is shown through first elongated branch 71. A guide wire 81 may be positioned into abdominal aorta 80 via patient femoral artery.

Catheter 85, 90 may then be advanced through an iliac artery 86, 87 and into abdominal aorta 80 along pre-positioned guide wire 81. Extension cuff 50 may then be positioned substantially within either elongated branch 71, 72 and trunk body 70 extending into the abdominal aorta 80. Extension cuff 50 position may be determined by visualization methods known in the art, such as fluoroscopy and/or intravascular ultrasound (IVUS). In one embodiment, radiopaque markers disposed on portion of the extension cuff 50 and/or catheter 85, 90 may be visualized by fluoroscopy.

After appropriate catheter 85, 90 positioning, extension cuff 50 may be deployed. Referring to FIG. 4A, a push rod 82 may be maintained in a fixed contact position with extension cuff 50 as catheter 85 is withdrawn axially. Referring to FIG. 4B, balloon of catheter 90 may be inflated to expand extension cuff 50. Extension cuff 50 may self-expand or balloon-expand to a deployed diameter, D1, into operable engagement with trunk body 70. The operable engagement may include frictional forces between contacting extension cuff 50 and trunk body 70 surfaces. Another portion of the extension cuff 50 (e.g. its proximal end) may be expanded into operable engagement with abdominal aorta 80 providing a seal with the vessel wall.

As catheter 85 is further withdrawn, or as catheter 90 is inflated, cuff branch may be deployed to diameter, D2, into operable engagement with one of the elongated branches 71, 72. Access port may expand to deployed diameter, D3. The access port may also operably engage the elongated branch 71, 72 contralateral to the cuff branch, given the access port extends into that elongated branch 71, 72 a sufficient length. The operable engagement may include frictional forces between contacting cuff branch/access port and elongated branch 71, 72 surfaces. The extension cuff, cuff branch, and access port deployed diameters, D1, D2, and D3, as well as their orientation, size, and geometry may vary as required by application. For example, the cuff branch may be deployed into either elongated branch 71, 72.

Figure 5:
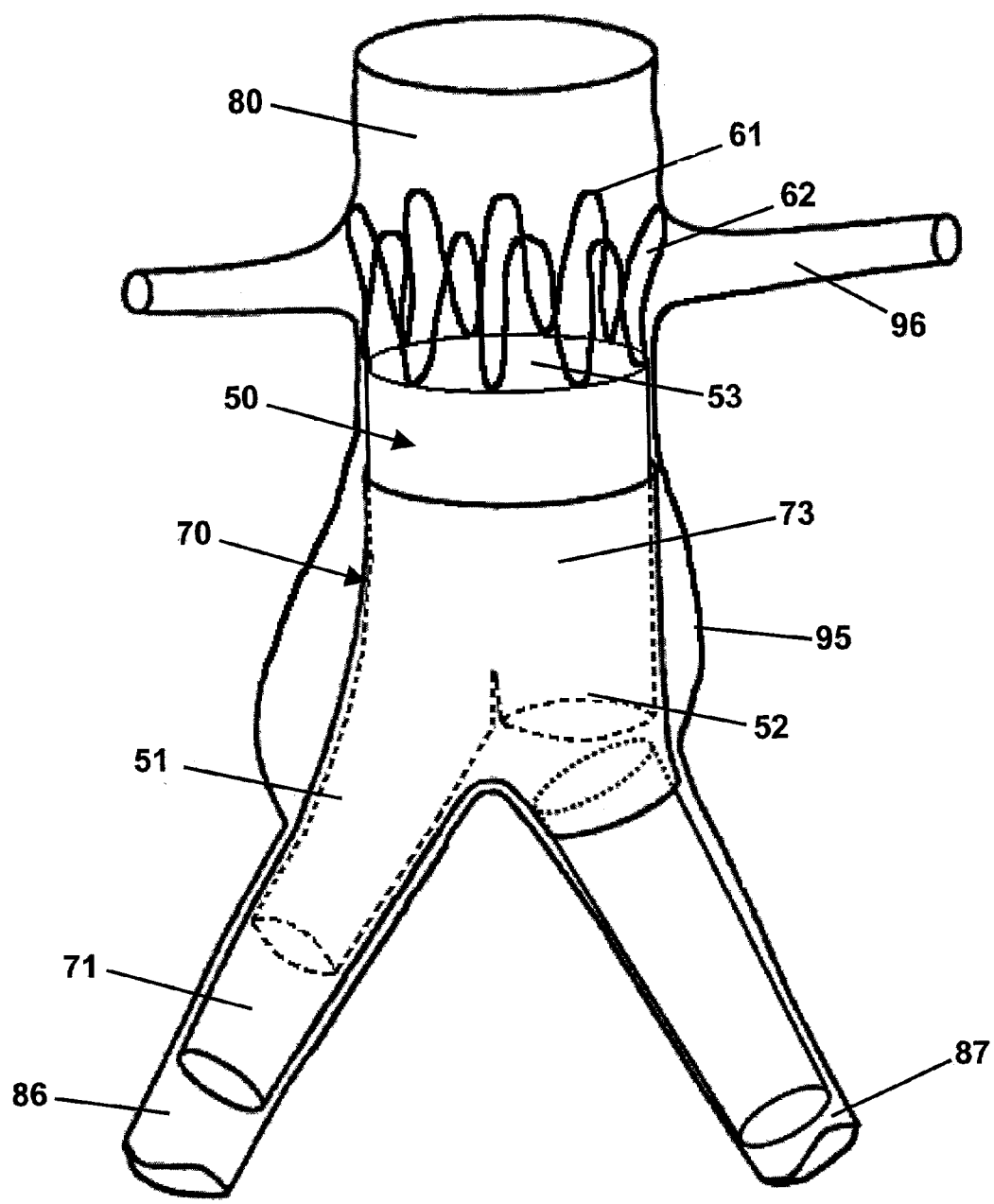
FIG. 5 is a view of the deployed endoluminal prosthetic assembly deployed in an abdominal aortic aneurysm.

Catheter 85, 90 and guide wire 81 may be removed from patient, leaving extension cuff 50 and trunk body 70 in the fully deployed state shown in FIG. 5. Cuff lumen 53 is in communication with the body lumen 73. Abdominal aorta 80 blood flow may enter the cuff lumen 53 and bifurcate into body lumen 73, optionally diverting through aperture or crown openings 62 into renal arteries 96. The blood flow may continue into each of the iliac arteries 86, 87 in a path that approximates that of a normal, healthy vascular system. In many cases, the trunk body 70-aorta 80 contact provides a fluid seal minimizing blood flow into aneurysm 95. Should the trunk body 70-aorta 80 seal fail, extension cuff 50 may be used to re-establish this seal thereby isolating an aneurysm 95 from the bloodstream.

A portion of the extension cuff 50 is retainably positioned within the trunk body 70, and a portion of the cuff branch 51 is retainably positioned within one of the elongated branches 71, 72. Additionally, a portion of the access port 52 may extend into (extension not shown) and be retainably positioned within the other elongated branch 71, 72. The extension cuff 50-trunk body 70, and the cuff branch 51 and access port 52-elongated branches 71, 72 operable engagements provides redundant retention forces. The retention forces may minimize extension cuff 50 disengagement from the trunk body 70. In addition, the crown 61 may provide an additional retention force to secure extension cuff to the aorta 80.

While the embodiments of the invention disclosed herein are presently considered to be preferred, various changes and modifications can be made without departing from the spirit and scope of the invention. For example, the bifurcated endoluminal prosthetic assembly configuration, and method of deploying the same are not limited to any particular design or sequence. Specifically, the trunk body, extension cuff, and associated components geometry, size, arrangement, number, material, features, method of expansion, orientation, and deployment step order may be varied without limiting the utility of a device according to the invention.

What is claimed is:

1. An endoluminal prosthetic assembly, comprising:
   a trunk body including first and second elongated branches, the trunk body and elongated branches including a bifurcated body lumen formed therein wherein the trunk body comprises a plurality of support elements; and
   an extension cuff including a cuff branch and an access port, the extension cuff, cuff branch, and access port including a bifurcated cuff lumen formed therein, wherein a portion of the extension cuff is retainably positioned within the trunk body, a proximal end of the extension cuff extends beyond the trunk body, a portion of the cuff branch is retainably positioned within one of the elongated branches, and the cuff lumen is in communication with the body lumen.

2. The assembly of claim 1 wherein the extension cuff comprises at least one aperture formed in the extension cuff allowing fluid flow through said aperture.

3. The assembly of claim 1 wherein the extension cuff comprises a crown portion operably attached to the extension cuff, wherein the crown allows fluid flow through crown openings formed therein.

4. The assembly of claim 3 wherein the crown comprises a crown diameter greater than a vessel diameter.

5. The assembly of claim 1 wherein the extension cuff comprises at least one marker.

6. The assembly of claim 1 wherein the extension cuff comprises a biocompatible membrane disposed on a support element.

7. The assembly of claim 1 wherein the extension cuff comprises an expandable extension cuff, wherein the expandable extension cuff expands from a collapsed form to an expanded ring form.

8. The assembly of claim 7 wherein the expandable extension cuff comprises a self expanding extension cuff.

9. The assembly of claim 7 wherein the expandable extension cuff comprises a balloon-expandable extension cuff.

10. The assembly of claim 7 wherein the expandable extension cuff comprises an extension cuff diameter greater than a trunk body diameter.

11. The assembly of claim 7 wherein the expandable extension cuff comprises a cuff branch diameter greater than a first elongated branch diameter.

12. A method of extending an endoluminal prosthetic assembly including a trunk body including first and second elongated branches deployed in a bifurcated vessel, comprising:
positioning a portion of a compressed extension cuff having a bifurcated cuff lumen within the trunk body and the first elongated branch;
positioning a proximal end of the extension cuff to extend beyond the trunk body; and
expanding the compressed extension cuff into operable engagement with a vessel wall, the trunk body and the first elongated branch.

13. The method of claim 12 wherein expanding the compressed extension cuff comprises self-expanding the extension cuff.

14. The method of claim 12 wherein expanding the compressed extension cuff comprises balloon-expanding the extension cuff.

15. The method of claim 12 wherein the operable engagement comprises frictional surface contact.

16. The method of claim 12 further comprising providing fluid egress through the extension cuff.

17. The assembly of claim 1 wherein the support elements are composed of a material selected from the group consisting of nitinol, titanium, tantalum, stainless steel, metal alloy and polymer.

18. An endoluminal prosthetic assembly, comprising:
a trunk body including a first and a second elongated branch, the trunk body comprising a plurality of support elements;
an extension cuff having a bifurcated cuff lumen retainably positioned within the trunk body and one of the elongated branches, wherein a proximal end of the extension cuff extends beyond the trunk body; and
a graft material disposed adjacent the trunk body.

19. The assembly of claim 18 wherein the plurality of support elements are composed of a material selected from the group consisting of nitinol, titanium, tantalum, stainless steel, metal alloy and polymer.

20. The method of claim 12 further comprising sealing the proximal end of the trunk body to the vessel wall.

* * * * *